United States Patent
Wittkampf et al.

[11] Patent Number: 6,134,463
[45] Date of Patent: Oct. 17, 2000

[54] ELECTROPHYSIOLOGY CATHETER WITH A BULLSEYE ELECTRODE

[75] Inventors: Frederick H. M. Wittkampf, Utrecht, Netherlands; Wilton W. Webster, Jr., Baldwin Park, Calif.

[73] Assignee: Cordis Webster, Inc., Baldwin Park, Calif.

[21] Appl. No.: 08/829,007

[22] Filed: Mar. 31, 1997

[51] Int. Cl.⁷ .............................. A61B 5/042; A61B 18/14
[52] U.S. Cl. ..................... 600/374; 600/393; 606/41; 607/99; 607/122
[58] Field of Search .................... 600/374, 393; 606/41, 48, 50; 607/122, 99

[56] References Cited

U.S. PATENT DOCUMENTS

| | | | |
|---|---|---|---|
| 3,920,021 | 11/1975 | Hiltebrandt | 606/50 |
| 4,784,161 | 11/1988 | Skalsky et al. | 607/122 |
| 4,848,352 | 7/1989 | Pohndorf et al. | 607/122 |
| 5,398,683 | 3/1995 | Edwards et al. | 128/642 |
| 5,718,701 | 2/1998 | Shai et al. | 606/41 |
| 5,782,760 | 7/1998 | Schaer | 606/41 |
| 5,836,875 | 11/1998 | Webster, Jr. | 606/50 |

FOREIGN PATENT DOCUMENTS

| | | | |
|---|---|---|---|
| 222207 | 5/1985 | Germany | 606/48 |
| WO93/08757 | 5/1993 | WIPO | |

*Primary Examiner*—Lee Cohen
*Attorney, Agent, or Firm*—Christie, Parker & Hale, LLP

[57] ABSTRACT

An electrode catheter for cardiac electrophysiology is provided. An elongated body suitable for intravascular insertion and forming an axial lumen is provided. A tip electrode defines an axial hole extending inward from a distal end of the tip electrode and is directly mounted to a distal end of the elongated body on a proximal end of the tip electrode. An eye electrode is located within the axial hole substantially concentric to and electrically insulated from the tip electrode. Electrode lead wires run through the axial lumen. One of the electrode lead wires is electrically connected to the eye electrode and another of the electrode lead wires is electrically connected to the tip electrode.

17 Claims, 9 Drawing Sheets

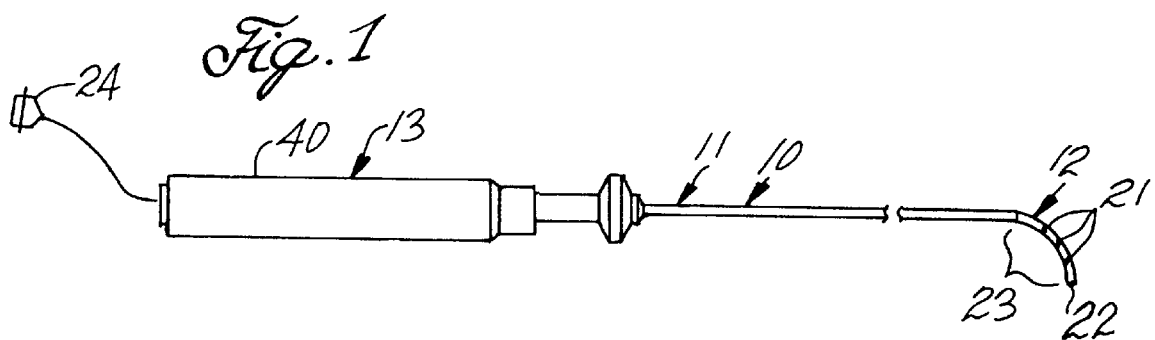
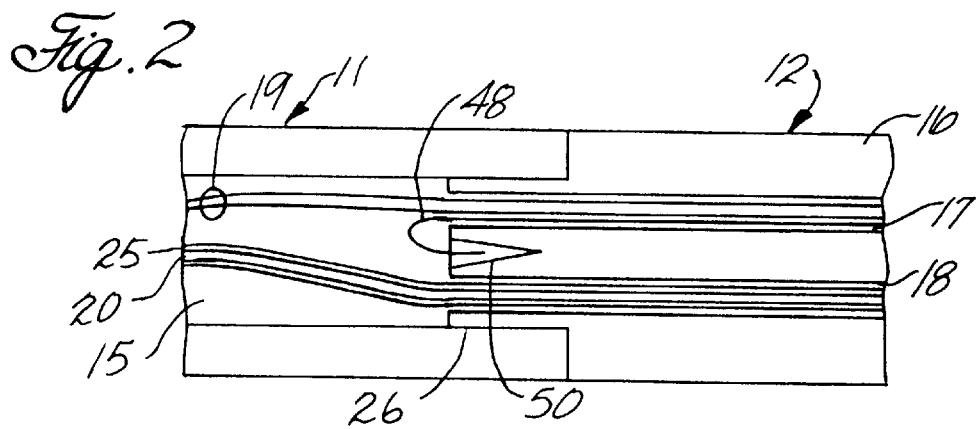
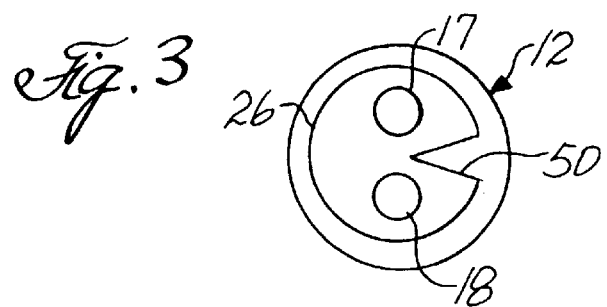

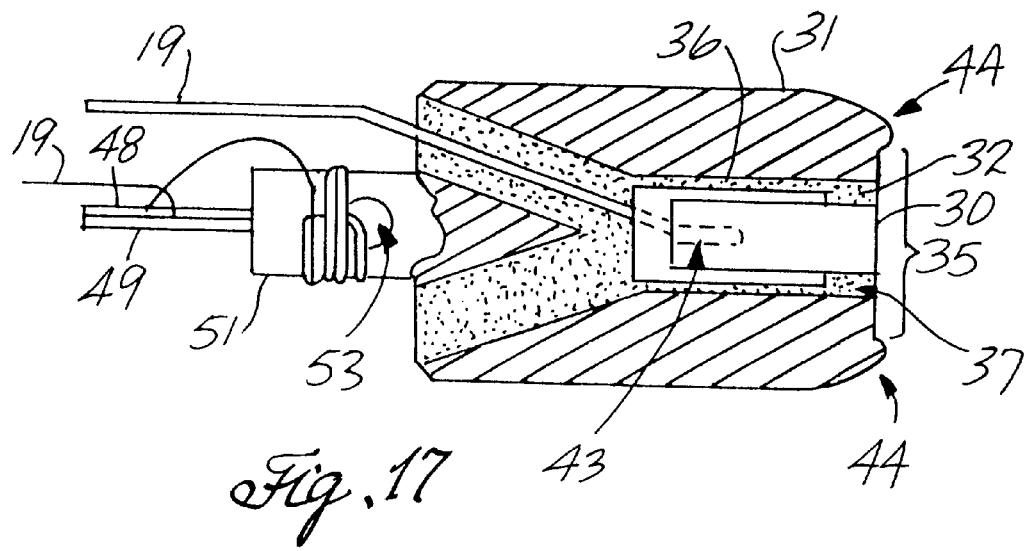
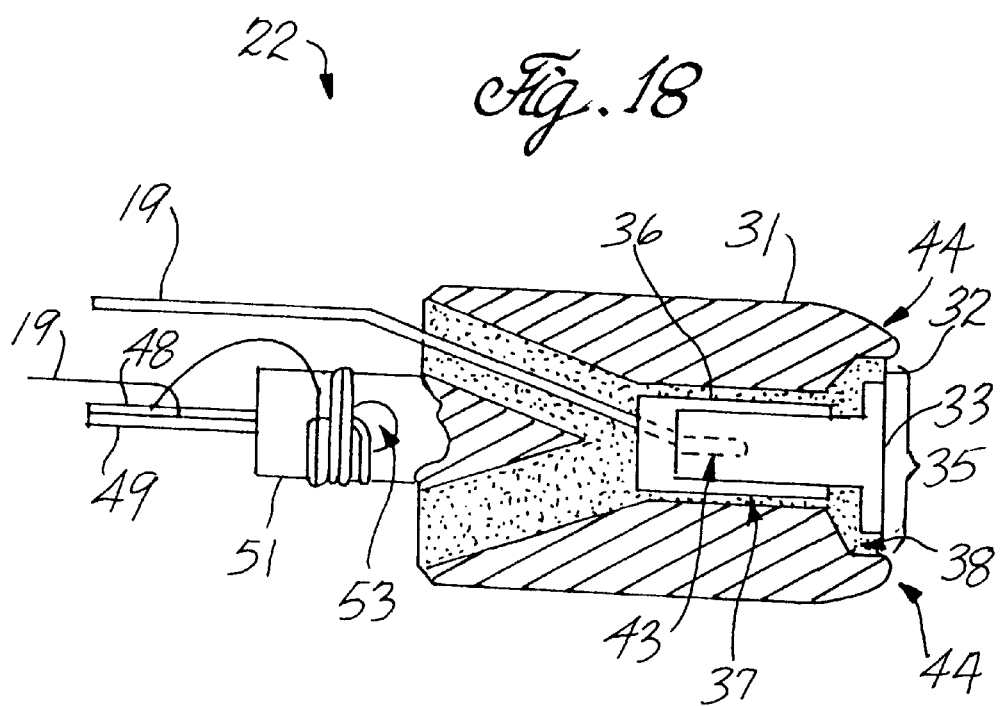

ELECTROPHYSIOLOGY CATHETER WITH A BULLSEYE ELECTRODE

FIELD OF THE INVENTION

This invention relates to an electrophysiology catheter having a bullseye electrode and more specifically, to an electrophysiology catheter having a bullseye electrode comprising an eye electrode located substantially concentric to a tip electrode.

BACKGROUND OF THE INVENTION

Electrophysiology is a specialty within the field of cardiology for the diagnosis and treatment of electrical abnormalities of the heart. Certain types of abnormalities are caused by acyclic electrical activity within the heart due to aberrant accessory atrioventricular pathways.

These include atrial flutter, atrial fibrillation and ventricular tachycardia.

These forms of cardiac disorders can be diagnosed using an electrophysiology catheter positioned at the ventricular side of the mitral annulus. A local bipolar electrogram is recorded and signals from recording electrodes in contact with endocardial tissue which are present at different locations are electrically averaged. However, during orthodromic tachycardia and in particular during ventricular stimulation, the direction of the ventricular activation sequence can be situated parallel to the recording dipole resulting in a large amplitude ventricular signal and therefore complicating the diagnosis procedure. Moreover, the detection of retrograde atrial activation in the wake of a large ventricular complex is further complicated by short ventricular-atrial conduction delays located near the accessory pathway resulting in a problematic recording of retrograde atrial activity when using a conventional catheter tip below the mitral annulus in patients with a concealed left side accessory pathway.

Once detected, these forms of cardiac disorders can be treated by destroying the causative heart tissue through radio frequency (RF) catheter ablation. Accessory pathways are ablated using an electrophysiology catheter guided into the heart through a vein or artery which is positioned at the site of the causative accessory pathway. RF energy sufficient to destroy heart tissue is emitted from the catheter tip and the ablated tissue is replaced by scar tissue which interrupts the accessory pathway and restores the normal conduction of electrical activity within the heart.

An electrophysiology diagnosis and ablation catheter with a high-performance filter system is shown in International Patent Application WO 92/21285, filed May 24, 1991 to S. D. Edwards et al. The catheter probe has a terminal tip portion with a tip electrode carried on its distal end. A reference electrode for supplying a reference potential signal is located 3–10 mm proximally from the tip electrode in the side of the catheter shaft. An ablating electrode for providing electromagnetic energy is located adjacent but electrically insulated from both the tip and reference electrodes. The tip and reference electrodes generate and record (map) monophasic action potentials while the ablating electrode ablates endocardial tissue. Since only the ablating electrode ablates, the size and formation of ablative injury is limited by the position and orientation of this sole electrode. Moreover, the reference electrode is preferably flush or recessed from the catheter shaft and only contacts blood, not endocardial tissue, thereby limiting its ability to detect retrograde atrial potentials.

Therefore, what is needed is an electrode catheter having an ablation electrode at its tip capable of performing both cardiac mapping and ablation of heart tissue thereby resulting in a more controllable lesion size and enhanced efficacy of treatment.

SUMMARY OF THE INVENTION

The present invention enables the above problems to be overcome and provides a bullseye electrode catheter.

An embodiment of the present invention is an electrode catheter for cardiac electrophysiology. An elongated body suitable for intravascular insertion and forming an axial lumen is provided. A tip electrode defines an axial hole extending inward from a distal end of the tip electrode and is directly mounted to a distal end of the elongated body on a proximal end of the tip electrode. An eye electrode is located within the axial hole substantially concentric to and electrically insulated from the tip electrode. Electrode lead wires run through the axial lumen. One of the electrode lead wires is electrically connected to the eye electrode and another of the electrode lead wires is electrically connected to the tip electrode.

Still other embodiments of the present invention will become readily apparent to those skilled in the art from the following detailed description wherein is shown and described only embodiments of the invention by way of illustration of the best modes contemplated for carrying out the invention. As will be realized, the invention is capable of other and different embodiments and its several details are capable of modification in various obvious respects, all without departing from the spirit and the scope of the present invention. Accordingly, the drawings and the detailed description are to be regarded as illustrative in nature and not as restrictive.

BRIEF DESCRIPTION OF THE DRAWINGS

FIG. 1 is a plan view of a preferred embodiment of a bullseye electrode catheter constructed in accordance with the present invention;

FIG. 2 is a cross-sectional view of the junction of the catheter body and the catheter tip;

FIG. 3 is a rear view of the proximal end of the catheter tip;

FIG. 17 is a cutaway view of the bullseye electrode taken along the line 17—17 in FIG. 14;

FIG. 18 is a cutaway view of the bullseye electrode with a large eye electrode taken along the line 18—18 in FIG. 15.

DETAILED DESCRIPTION

Figure 4A:
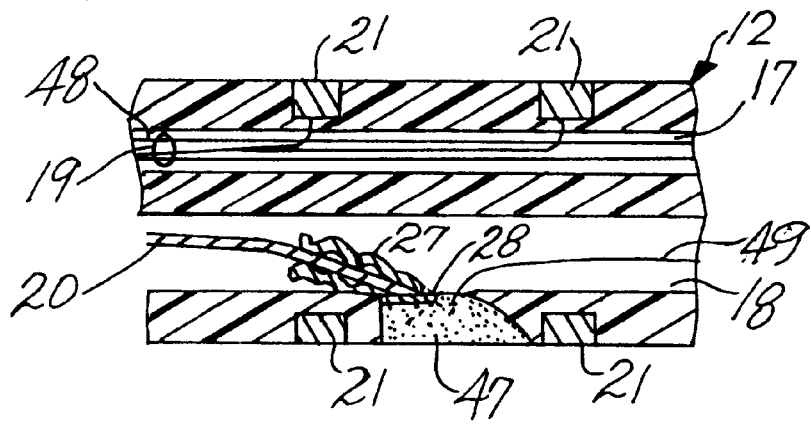
FIG. 4A is a cross-sectional view of the puller wire and safety wire attachments to the wall of the catheter tip.

A preferred embodiment of a bullseye electrode catheter constructed in accordance with the present invention is shown in FIG. 1. The bullseye electrode catheter 10 comprises an elongated catheter body 11, a catheter tip 12 at the distal end of the catheter body 11 and a control handle 13 at the proximal end of the catheter body 11. These components will now be discussed.

I. Catheter Body

A cross-sectional view of the junction of the catheter body 11 and the catheter tip 12 is shown in FIG. 2. The catheter body 11 comprises an elongated, tubular section forming a central lumen 15. The catheter body 11 is flexible but substantially non-compressible along its longitudinal length. The catheter body 11 can be of any construction suitable for intravascular insertion and made of any flexible, electrically insulating material. In the described embodiment, a nylon tube surrounded by one or more reinforcing layers of braided stainless steel or similar materials with a polyurethane coating is preferred, such as described in U.S. Pat. No. 5,057,092, the subject of which is incorporated herein by reference.

The catheter body 11 surrounds a plurality of electrode lead wires 19 and a puller wire 20, both extending from the control handle 13 inside the central lumen 15 for the entire length of the catheter body 11 into the catheter tip 12. In the described embodiment, each of the lead wires 19 are preferably constructed of #38 copper wire having a diameter of about 0.004 inches. The puller wire 20 is preferably constructed of stainless steel wire surrounded by a Teflon sheath 25 or the like for lubricity and for keeping the puller wire 20 generally coaxial with the catheter body 11, such as described in U.S. Pat. Nos. 4,960,134 and Re. 34,502, the subjects of which are incorporated herein by reference.

The length and diameter of the catheter body 11 are not critical and can vary according to the particular application. For the electrode catheter shown, a length of about 40 to 48 inches, an outer diameter of about 0.065 to 0.100 inches (approximately 5 to 8 French) and an inner diameter of about 0.030 to 0.040 inches are preferred.

II. Control Handle

Referring again to FIG. 1, the control handle 13 comprises a generally cylindrical housing 40 having open chambers at each end. The housing is generally symmetrical about its longitudinal axis to allow the control handle to be freely rotated without altering quality of control or convenience. The catheter body 11 is fixedly attached to the control handle 13 through one of the open chambers at one end of the control handle 13 and a molded multi-pin connector 24 is electrically connected to the control handle 13 at its other end. The control handle 13 can be plugged directly into a simulator, recorder or other electrical device. Alternatively, the connector 24 can be connected to the female end of a floating extension cable which in turn has connectors at its opposite end which can be plugged into an electrical device such as described above.

Any suitable control handle 13 which can control the longitudinal movement of the puller wire (further described hereinbelow) relative to the catheter body 11 can be used. A preferred control handle and manner of fixedly attaching the catheter body 11, mounting the puller wire 20 and connecting the electrode lead wires 19 are described in U.S. Pat. Nos. 4,960,134 and Re. 34,502, the subjects of which are incorporated herein by reference.

III. Catheter Tip

Also shown in FIG. 1, the catheter tip 12 comprises a steerable section 23, a plurality of ring electrodes 21 and a bullseye electrode 22. These will now be discussed.

A. Steerable Section

Referring again to FIG. 2, the steerable section 23 of the catheter tip 12 comprises a short section of flexible tubing 16 forming a pair of non-overlapping, side-by-side lumens, upper lumen 17 and lower lumen 18. These lumens are longitudinally situated off-axis and are not coaxial with the catheter tip 12. The central lumen 15 of the catheter body 11 is in communication with both the upper lumen 17 and the lower lumen 18 of the catheter tip 12. The flexible tubing 16 can be made of any suitable material and is preferably more flexible than the catheter body. In the described embodiment, the preferred material is polyurethane having a D55 hardness, such as described in U.S. Pat. Nos. 5,057,092; 4,960,134 and Re. 34,502, the subjects of which are incorporated herein by reference.

The diameter of the catheter tip 12 is not critical but is preferably about the same as or slightly smaller than the diameter of the catheter body 11. Likewise, the length of the catheter tip 12 is not critical. In the described embodiment, the length of the catheter tip 12 is about three inches but other suitable lengths are possible depending on the particular purpose.

A pair of safety wires 48 (shown in FIG. 2) and 49 (shown in FIG. 4) are used to secure the bullseye electrode 22 to the catheter tip 12. In the described embodiment, each of the safety wires 48 and 49 are preferably constructed of Monel 400 wire having a diameter of about 0.0065 inches. Attachment of the ends of the pair of safety wires 48 and 49 is further described hereinbelow.

A preferred means for attaching the catheter tip 12 to the catheter body 11 is also shown in FIG. 2. The proximal end of the catheter tip 12 comprises an outer circumferential reduced diameter 26 sized to allow the proximal end of the catheter tip 12 to be snugly inserted into the distal end of the catheter body 11. The catheter tip 12 is fixedly attached to the catheter body 12 by glue or the like. The circumferential reduced diameter 26 can additionally be tapered (not shown) at its proximal end to allow for easier insertion into the distal end of the catheter body 11. In the described embodiment, the electrode lead wires 19 and the safety wire 48 are inside the upper lumen 17 and the puller wire 20 is inside the lower lumen 18.

A rear view of the proximal end of the catheter tip 12 is shown in FIG. 3. A notch 50 for securing the safety wire 48 into place is formed to run axially along one surface of the circumferential notch 26. The notch 50 is situated approximately equidistant between the upper lumen 17 and the lower lumen 18 and tapers upwards in the longitudinal direction away from the proximal end of the catheter tip 12. The length of the notch 50 must be less than the width of the circumferential notch 26. The safety wire 48 (see FIG. 2)

extends through the catheter tip 12 from the bullseye electrode 22. At the proximal end of the flexible tubing 16, the safety wire 48 is bent backwards and fit into the notch 50. The safety wire 48 is securely fixed into place when the notched proximal end of the catheter tip 12 is inserted into the distal end of the catheter body 11. In the described embodiment, the notch 50 is about 0.080 inches long.

The catheter tip 12 is steerable by means of the puller wire 20 which is fixedly attached at its proximal end to the control handle 13 and at its distal end to the short section of flexible tubing 16. By extending the puller wire 20 through the lower lumen 18, the puller wire 20 is positioned eccentrically to the axis of the catheter body 11. Rearward movement of the puller wire 20 in the proximal direction relative to the catheter body 11 by manipulation of the control handle 13 results in a curving of the catheter tip 12. Such curving can be used to steer the electrode catheter during cardiac electrophysiology. An example of such a puller wire construction is disclosed in U.S. Pat. Nos. 4,960,134 and Re. 34,502, the subjects of which are incorporated herein by reference.

Figure 4B:
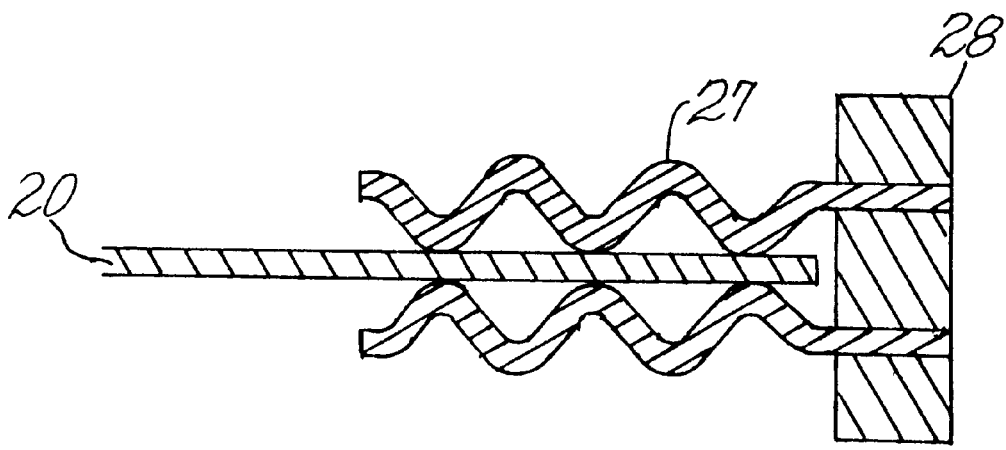
FIG. 4B is a cross-sectional view of the puller wire, crimping tube, crossbar assembly.

A preferred means for attaching the puller wire 20 and the safety wire 49 to the wall of the catheter tip 12 is shown in the cross-sectional views of FIG. 4A and FIG. 4B. A notch 47 is made in the side of the catheter tip 12 into lower lumen 18. The distal end of the puller wire 20 is passed through the notch 47 to the outside of the catheter tip 12. A crimping tube 27 is then fitted over and fixedly secured to the distal end of the puller wire 20. The crimping tube 27 is preferably a 4 mm long section of a hollow 27 gage hypodermic needle. The distal end of the puller wire 20 is inserted into the crimping tube and multiple crimps are made to secure the puller wire. The puller wire is then soldered therein. A crossbar 28 is then welded onto the distal end of the crimping tube 27. The crossbar 28 is wider than the opening from the notch 47 into the lower lumen 18 such that the crossbar 28 cannot fit inside the lower lumen 18.

The safety wire 49 is bent backwards into the notch 47. Both the crossbar 28 and the safety wire 49 are situated within a notch 47 in the wall of the flexible tubing 16 which extends into the lower lumen 18. The crossbar 28 and the safety wire 49 are positioned inside the notch and electrical contact between them is avoided. The portion of the notch 47 not filled by the crossbar 27 and the safety wire 49 are filled with glue or the like, preferably a polyurethane glue harder than the material of the flexible tubing 16. Any rough edges of the crossbar 28, the safety wire 49 and the filler material are polished to provide a smooth, continuous surface with the outer surface of flexible tubing 16.

In the described embodiment, the crossbar 27 is constructed from stainless steel and is crimped to the puller wire 20 by any conventional technique, such as described in U.S. Pat. Nos. 4,960,134 and Re. 34,502, the subjects of which are incorporated herein by reference. Preferably, the crossbar 27 has a crosspiece about 0.020 inches wide and a stem about 0.160 inches long.

B. Ring Electrodes

Referring again to FIG. 1, along the length of the flexible tubing 16, there are a plurality of ring electrodes 21 for recording intercardiac signals. Each of the ring electrodes 21 is shaped like a ring having an outer diameter about the same as that of the flexible tubing 16 so that a smooth, continuous surface is formed. In the described embodiment, each ring electrode 21 has an outer diameter of about 6½ French and is preferably constructed from platinum or alloys of platinum and iridium. Each ring electrode 21 is electrically connected (as shown in FIG. 4) to one of the electrode lead wires 19 by any conventional technique.

C. Bullseye Electrode

The bullseye electrode 22 is mounted on the distal end of the catheter tip 12. As shown in the side view of FIG. 5, the bullseye electrode 22 comprises an eye electrode 30 and a tip electrode 31 each electrically attached by any conventional technique to an associated electrode lead wire 19 as further described hereinbelow. The eye electrode 30 and the tip electrode 31 can be of any suitable construction and are preferably made of platinum or alloys of platinum and iridium. The eye electrode 30 and the tip electrode 31 are separated from each other by insulation 32 which in the described embodiment is preferably cured liquid polyurethane.

The eye electrode 30 is for performing both ablation and mapping and is located substantially concentric to and along an axis of the tip electrode 31. The eye electrode 30 provides an extra recording opportunity by increasing the magnitude of local electrical events and by unmasking local electrical events at the distal end of the catheter tip 12 that are otherwise lost due to short circuiting in the tip electrode 31. Such data is electrophysiologically valuable and in particular useful for detecting retrograde atrial potentials.

The combination of the eye electrode 30 and the tip electrode 31 has many benefits. First, a recording dipole is created closer to the atrial myocardium and this smaller dipole can record electrograms more representative of electrophysiological events occurring in close vicinity to the bullseye electrode 22. Also, the ablative properties of the bullseye electrode 22 are not compromised since both the eye electrode 30 and the tip electrode 31 can be used for ablation, especially since both are generally in contact with endocardial tissue.

Figure 5:
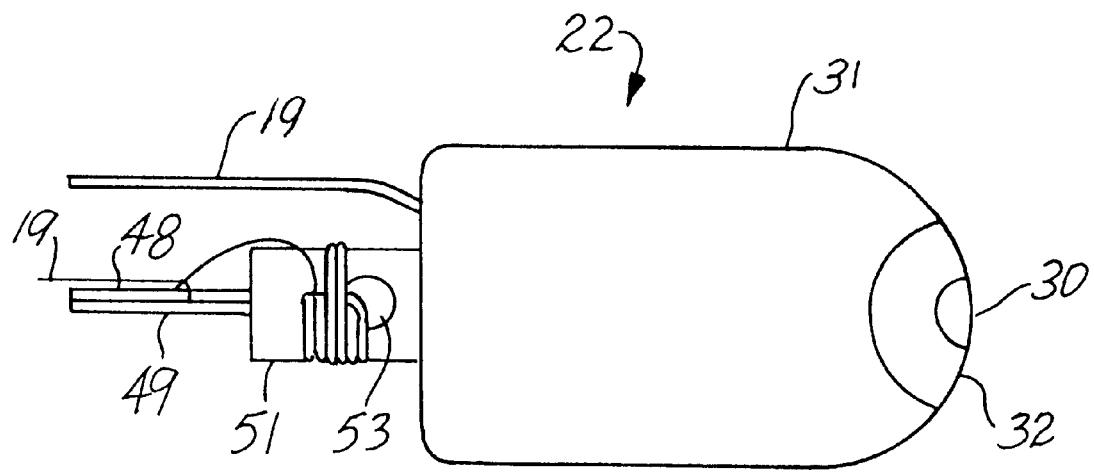
FIG. 5 is a side view of a bullseye catheter tip with a small eye electrode constructed in accordance with the present invention.
Figure 7:
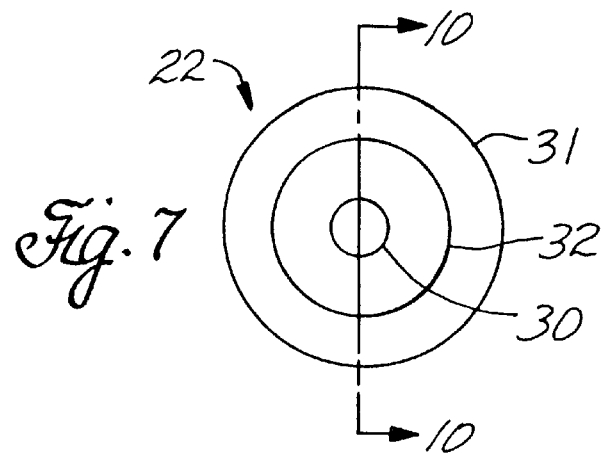
FIG. 7 is a front view of the bullseye electrode of FIG. 5.
Figure 8:
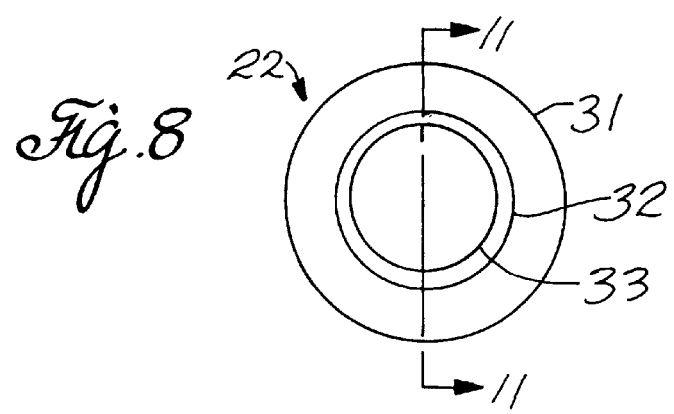
FIG. 8 is a front view of the bullseye electrode with a large eye electrode.
Figure 9:
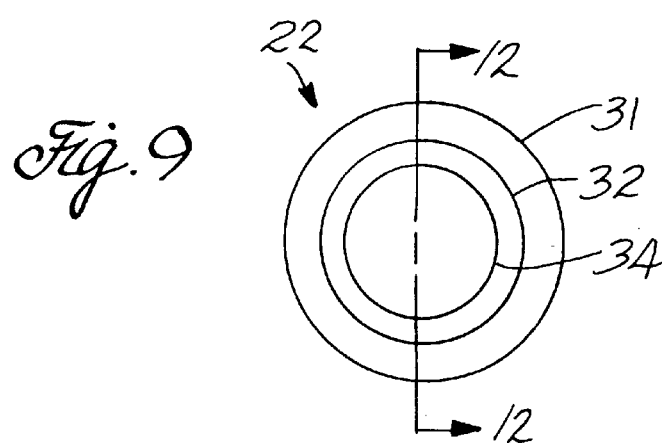
FIG. 9 is a front view of the bullseye electrode with a 45° eye electrode.
Figure 10:
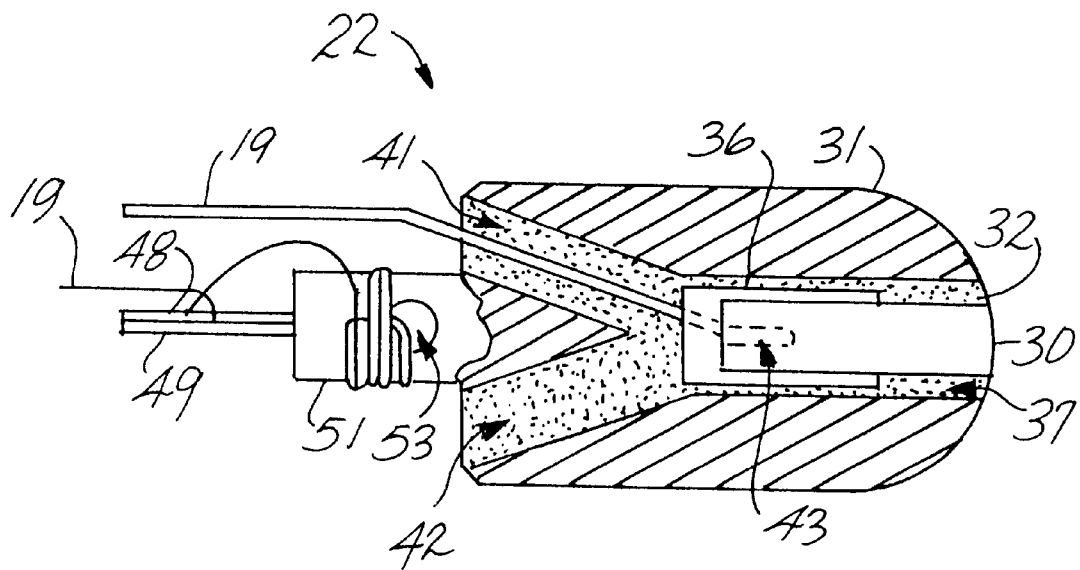
FIG. 10 is a cutaway view of the bullseye electrode taken along the line 10—10 in FIG. 7.
Figure 11:
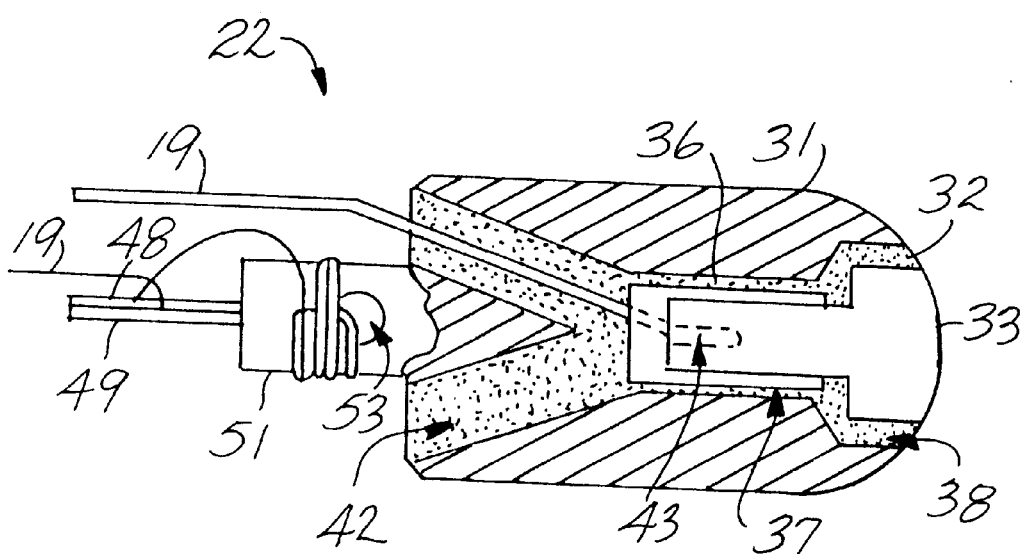
FIG. 11 is a cutaway view of the bullseye electrode with a large eye electrode taken along the line 11—11 in FIG. 8.
Figure 12:
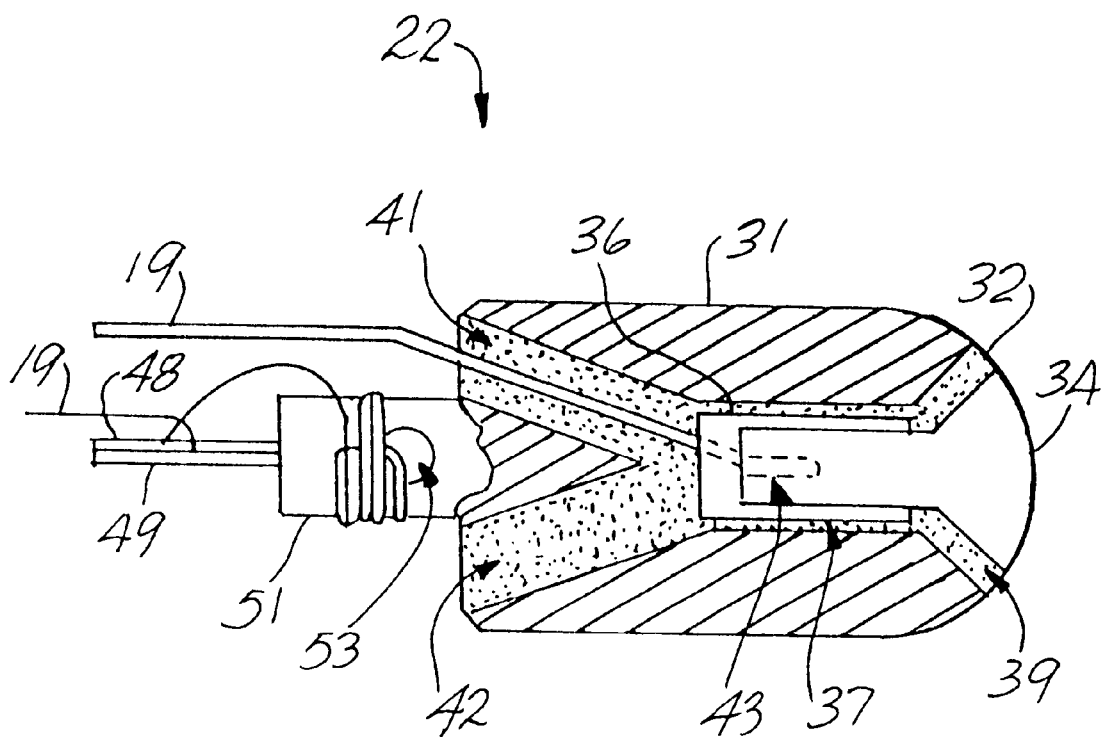
FIG. 12 is a cutaway view of the bullseye electrode with a 45° eye electrode taken along the line 12—12 in FIG. 9.

A front view of the bullseye electrode 22 of FIG. 5 with a small eye electrode 30 is shown in FIG. 7. Two further embodiments of the bullseye electrode 22 are shown in FIGS. 8 and 9 with a large eye electrode 33 and a 45° eye electrode 34, respectively. Cutaway views of the bullseye electrodes of FIGS. 7, 8 and 9 taken along the lines 10—10, 11—11, and 12—12 are shown in FIGS. 10, 11 and 12, respectively. In the discussion that follows, particular reference is made to the embodiment of the bullseye electrode 22 with a small eye electrode 30. However, this discussion applies equally to the further embodiments of the bullseye electrode 22 with a large eye electrode 33 or a 45° eye electrode 34.

An axial bore 37 is formed along an axis of the tip electrode 31 extending from its distal end inward. An electrode lead hole 41 and a potting vent hole 42 (discussed further hereinbelow) are formed in the proximal end of the tip electrode 31. The electrode lead hole 41 has a diameter of about 0.022 inches and is approximately 3 mm deep. The potting vent hole 42 has the same diameter and is at a depth that intersects the electrode lead hole 41. The axial bore 37 has a diameter of about 0.050 inches and is drilled to intersect the electrode lead hole 41 and the potting vent hole 42.

Referring to FIG. 10, the small eye electrode 30 is substantially cylindrical and situated within the axial bore 37 substantially concentric to the tip electrode 31. The small eye electrode 30 is electrically insulated from the tip electrode 31 by insulation 32, preferably cured liquid polyurethane. An electrode lead wire 19 is fixedly attached to the small eye electrode 30. In the described embodiment, lead wire hole 43 for attaching the electrode lead wire 19 is formed along the axis of the small eye electrode 30 at its proximal end. The electrode lead wire 19 is fed into the lead wire hole 43 and is preferably soldered into place.

In the described embodiment, the small eye electrode 30 has a diameter of about 0.040 inches and a length of about 2 mm. The lead wire hole 43 has a diameter of about 0.016 inches and is approximately 1 mm deep. The small eye electrode 30 is substantially centered within the axial bore 37 and fixed in place with insulation 32 as described above. Optionally, a polyamide insulating sleeve 36 can be placed substantially concentric to the tip electrode 31 for providing further insulation.

A bullseye electrode 22 with a large eye electrode 33 is shown in FIG. 11 which replaces the small eye electrode 30 with a large eye electrode 33. This embodiment requires a secondary axial bore 38 formed at the distal end of the tip electrode 31 to accommodate the larger distal end of the large eye electrode 33.

A bullseye electrode 22 with a 45° eye electrode 34 is shown in FIG. 12 which replaces the small eye electrode 30 with a 45° eye electrode 34. This embodiment requires a secondary 45° bore 39 formed at the distal end of the tip electrode 31 to accommodate the larger distal end of the 45° eye electrode 34.

Figure 13:
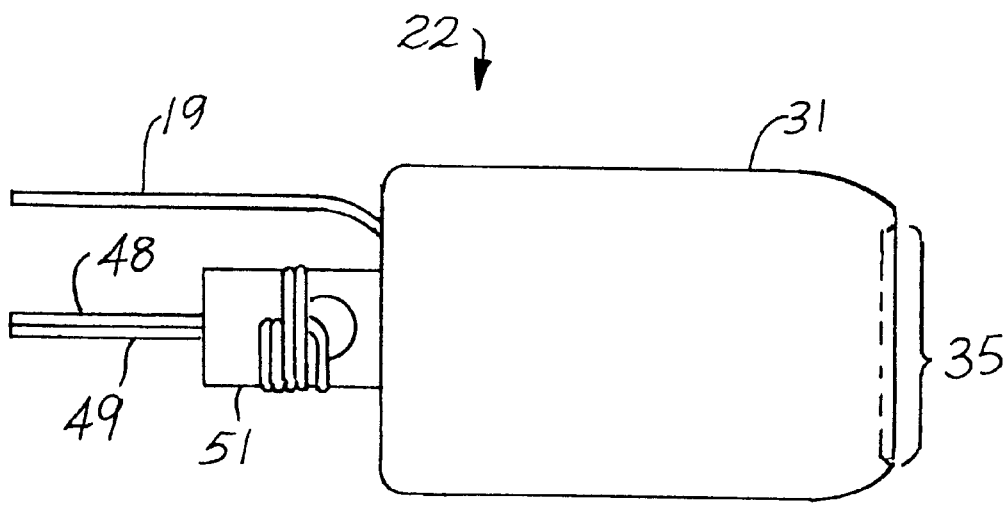
FIG. 13 is a cutaway view of a bullseye catheter tip with a recessed small eye electrode constructed in accordance with a further embodiment of the present invention.

Referring to FIG. 13, a further embodiment comprising a bullseye electrode 22 with a recessed small eye electrode 30 is shown. A recess 35 is formed in the distal end of the tip electrode 31 which offsets the contacting surface of the eye electrode 30 at its distal end inward towards the proximal end of the tip electrode 31. Although shown as a flat recessed surface, the recess can also be dished to form a concave surface (not shown).

Figure 14:
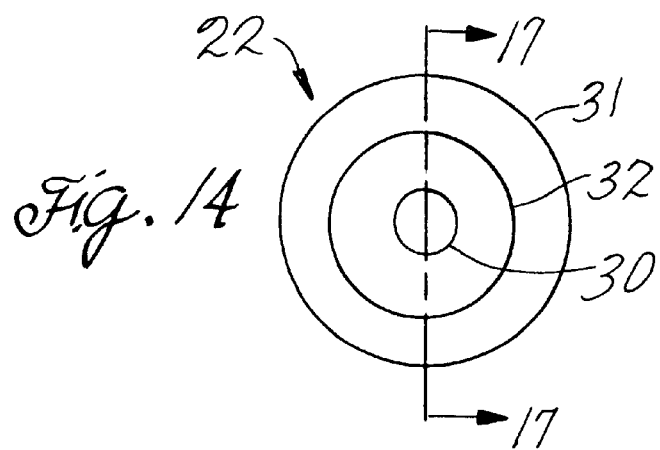
FIG. 14 is a front view of the bullseye electrode of FIG. 13.
Figure 15:
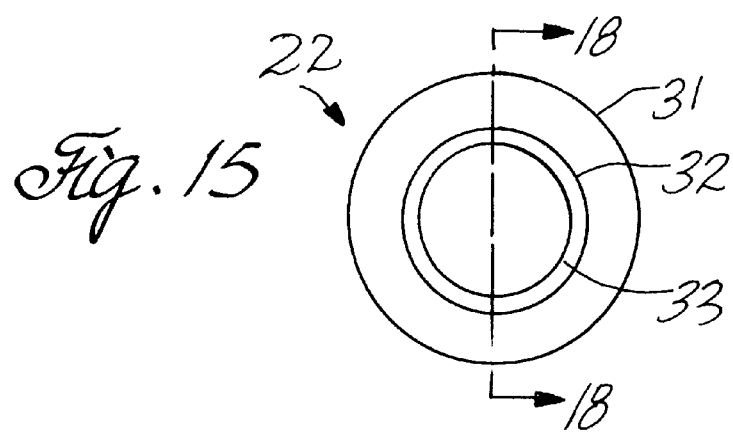
FIG. 15 is a front view of the bullseye electrode with a recessed large eye electrode.
Figure 16:
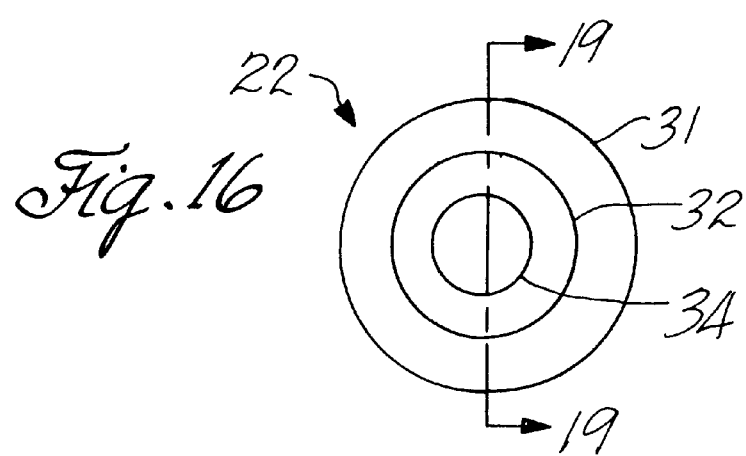
FIG. 16 is a front view of the bullseye electrode with a recessed 45° eye electrode.
Figure 19:
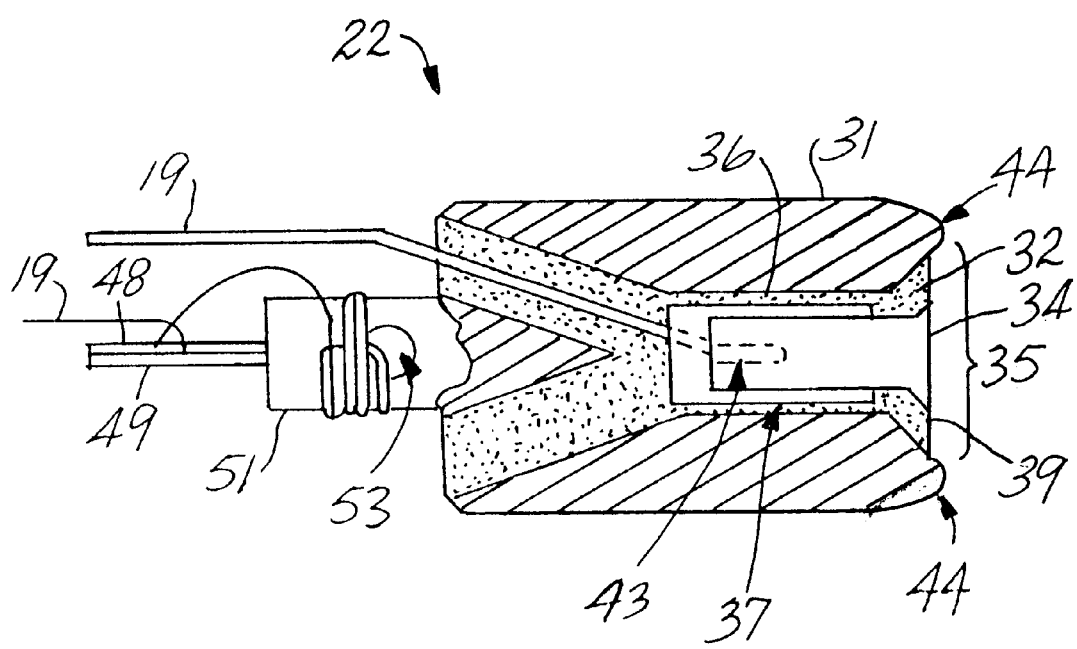
FIG. 19 is a cutaway view of the bullseye electrode with a 45° eye electrode taken along the line 19—19 in FIG. 16.

A front view of three further embodiments of the bullseye electrode with a recessed tip electrode are shown in FIGS. 14, 15 and 16 with a small eye electrode 30, a large eye electrode 33 and a 45° eye electrode 34, respectively. Cutaway views of the bullseye electrodes 22 of FIGS. 14, 15 and 16 taken along the lines 17—17, 18—18 and 19—19 are shown in FIGS. 17, 18 and 19, respectively. The distal ends of the tip electrode 31 formed by the axial bore 37, the secondary axial bore 38 and the 45° bore 39 are rounded to create rounded ends 44. The respective eye electrodes are set back, in the described embodiment approximately 1 mm, from the plane formed by the distal ends of the rounded ends 44. The recess 35 is thereby formed.

In a still further embodiment, a thermistor or thermocouple (not shown) can be mounted in the electrode lead hole 41. This enables further monitoring of the temperature of the bullseye electrode 22.

The pair of safety wires 48 and 49 and an electrode lead wire 19 are fixedly attached to the stem 51. Each of the safety wires 48 and 49 are inserted into the axial bore 52 and passed back out through the orifice 53. The safety wires 48 and 49 are then wrapped about 1.5 times around the stem 51. An electrode lead wire 19 is wrapped once around either of the safety wires and is then wrapped about two or three times around the stem 51 between the pair of safety wires 48 and 49 in a direction opposite from the safety wires. The electrode lead wire 19 and safety wires 48 and 49 are fixedly secured into place.

In the described embodiment, the safety wires and electrode lead wire preferably are soldered onto the stem 51. Also, the preferred solder comprises a composition of about 4% silver and 96% tin. A soldering flux, such as Stay Clean flux, is applied. The completed cup electrode 33 is ultrasonically defluxed in 70% isopropyl alcohol.

Figure 6:
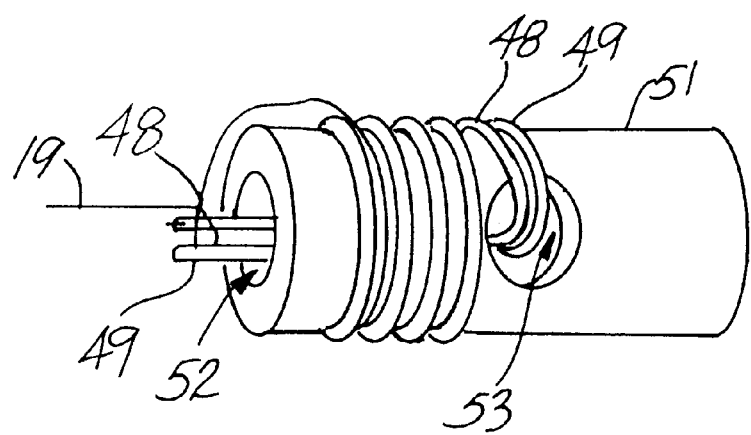
FIG. 6 is a rear perspective view of the stem with the safety wires and the electrode lead wire attached.

A stem 51 is formed on the proximal end of the tip electrode 31 for securing the bullseye electrode 22 to the distal end of the catheter tip 12. A rear perspective view of the stem 51 is shown in FIG. 6. An axial bore 52 is formed in the stem 51 with an orifice 53 intersecting perpendicular to an axis of the axial bore 52.

A presently preferred construction of the bullseye electrode 22 comprises modifying a 7FR tip electrode, part no. 5203-07, manufactured by Cordis Webster Inc., Baldwin Park, Calif. The tip electrode 31 is machined to the preferred outer dimensions (described further hereinbelow), the electrode lead hole 41 and the potting vent hole 42 are drilled into its proximal end and the axial bore 37 is drilled into its distal end. The electrode lead hole 41 and the potting vent hole 42 are coplanar along their axes and are angled about 30° from the axis of the tip electrode 31. The electrode lead hole 41 is used as a conduit for connecting an associated electrode lead wire 19 to the eye electrode. The potting vent hole 42 is used for facilitating the application of uncured liquid insulation into the axial bore 37 and is optional. A secondary axial bore 38 is drilled into a distal end of the tip electrode 31 for the bullseye electrode 22 with a large eye electrode 33 and a 45° bore 39 is drilled into a distal end of the tip electrode 31 for the bullseye electrode 22 with a 45° eye electrode 34. In the further embodiment of the bullseye electrode 22 having a recessed eye electrode, the rounded ends 44 are formed by rounding off the edges of the respective bores at their intersection with the distal end of the tip electrode 31.

For the tip electrode 31, the preferred overall length is about 4 mm and the preferred overall diameter is about 0.092+0.001 or −0.002 inches.

The bullseye electrode 22 is fixedly attached to the distal end of the catheter tip 12, preferably by glue or similar material. A preferred means for attachment is described in U.S. Pat. Nos. 4,960,134 and Re. 34,502, the subjects of which are incorporated herein by reference.

In practice, the present invention is ideal for mapping the heart and ablating accessory pathways causing arrhythmias. An electrophysiologist inserts the distal end of the catheter into a vein or artery and advances the tip into the heart. The heart is then mapped using the eye electrode, tip electrode and ring electrodes on the catheter. Once an accessory pathway is found, the electrophysiologist places the distal end of the catheter adjacent to the pathway. By using the eye electrode and tip electrode, the electrophysiologist can confirm that the distal tip is located directly adjacent to the pathway. RF energy is applied to the eye electrode and tip electrode simultaneously. The close spacing of the eye electrode and tip electrode allow for these electrodes to function as one continuous ablation electrode and the lesion created by the RF energy will be continuous.

The bullseye electrode 22 is capable of retrograde mapping and ablation of concealed accessory pathways. It is also capable of picking up Kent potentials in patients with anterograde conduction. The ring electrodes enable a comparison of standard unipolar and bipolar signals from the tip electrode 31 and a ring electrode 21 by short circuiting the tip electrode 31 and eye electrode 30. Thus, additional unipolar and bipolar electrograms oriented from the eye electrode 30 to the tip electrode 31 can be obtained from the same accessory pathway position.

The preceding description has been presented with references to presently preferred embodiments of the invention as shown in the drawings. Persons skilled in the art and technology to which this invention pertains will appreciate that alterations and changes in the described structures can be practiced without meaningfully departing from the principle, spirit and scope of this invention.

Accordingly, the foregoing description should not be read as pertaining only to the precise structures described and shown in the accompanying drawings, but rather as consistent with and as support for the following claims which are to have their fullest and fairest scope.

What is claimed is:

1. An electrode catheter for cardiac electrophysiology comprising:

an elongated body suitable for intravascular insertion, the elongated body including an axial lumen;

a tip electrode mounted to the elongated body, the tip electrode including a distal end defining an axial hole;

an eye electrode made of a polarizable material located within the axial hole substantially concentric to and electrically insulated from the tip electrode;

a first electrode lead wire extending through the axial lumen and electrically connected to the eye electrode; and a second electrode lead wire extending through the axial lumen and electrically connected to the tip electrode.

2. An electrode catheter according to claim 1, wherein the distal end of the tip electrode further defines a dished recess and the eye electrode defines a dished tip such that the dished recess and the dished tip together form a concave surface.

3. An electrode catheter according to claim 1, further comprising a safety wire securing the tip electrode to the elongated body.

4. An electrode catheter according to claim 1, wherein the tip electrode the and eye electrode form a concave surface.

5. An electrode catheter according to claim 1, wherein the tip electrode and the eye electrode form a recessed surface.

6. An electrode catheter according to claim 1, wherein the tip electrode and the eye electrode form a convex surface.

7. An electrode catheter according to claim 1, further comprising a thermal sensor mounted in the tip electrode.

8. An electrode catheter according to claim 7, wherein the thermal sensor comprises a thermocouple.

9. An electrode catheter according to claim 7, wherein the thermal sensor comprises a thermistor.

10. An electrode catheter according to claim 1, wherein the eye electrode comprises platinum.

11. An electrode catheter according to claim 1, wherein the eye electrode comprises platinum and iridium.

12. A steerable electrode catheter tip for cardiac electrophysiology comprising:

a tip electrode including a distal end defining an axial hole;

an eye electrode made of a polarizable material located within the axial hole substantially concentric to the tip electrode, the tip electrode and eye electrode defining an annular space;

insulation material placed in the annular space for electrically insulating the eye electrode from the tip electrode;

a first electrode lead wire electrically connected to the tip electrode;

a second electrode lead wire electrically connected to the eye electrode; and means for steering the catheter tip.

13. An electrode catheter tip according to claim 12, wherein the tip electrode and the eye electrode form a concave surface.

14. An electrode catheter tip according to claim 12, wherein the tip electrode and the eye electrode form a recessed surface.

15. An electrode catheter tip according to claim 12, wherein the tip electrode and the eye electrode form a convex surface.

16. A steerable electrode catheter tip according to claim 12, wherein the eye electrode comprises platinum.

17. A steerable electrode catheter tip according to claim 12, wherein the eye electrode comprises platinum and iridium.

* * * * *